United States Patent
Kaliki et al.

(10) Patent No.: US 8,591,599 B1
(45) Date of Patent: Nov. 26, 2013

(54) ELECTRODE ASSEMBLIES FOR DETECTING MUSCLE SIGNALS IN A PROSTHETIC LINER

(75) Inventors: Rahul R. Kaliki, Baltimore, MD (US); Neha Malhotra, Burbank, CA (US); Girish Singhal, Baltimore, MD (US); Nitish V. Thakor, Clarksville, MD (US)

(73) Assignee: Infinite Biomedical Technologies, LLC, Baltimore, MD (US)

( * ) Notice: Subject to any disclaimer, the term of this patent is extended or adjusted under 35 U.S.C. 154(b) by 225 days.

(21) Appl. No.: 12/987,035

(22) Filed: Jan. 7, 2011

(51) Int. Cl.
*A61F 2/70* (2006.01)
*A61B 5/04* (2006.01)
*A61F 2/80* (2006.01)
*A61F 2/66* (2006.01)

(52) U.S. Cl.
USPC ............... 623/25; 600/372; 600/546; 623/36; 623/57

(58) Field of Classification Search
USPC ......... 600/372, 382, 384, 386, 388, 390, 393, 600/546–547; 623/24–25, 36–37, 58–65
See application file for complete search history.

(56) References Cited

U.S. PATENT DOCUMENTS

| | | | |
|---|---|---|---|
| 3,631,542 A * | 1/1972 | Potter | 623/25 |
| 5,336,269 A | 8/1994 | Smits | |
| 5,443,525 A | 8/1995 | Laghi | |
| 6,500,210 B1 | 12/2002 | Sabolich et al. | |
| 6,702,858 B2 | 3/2004 | Christensen | |
| 6,740,123 B2 * | 5/2004 | Davalli et al. | 623/24 |
| 7,670,385 B2 | 3/2010 | Klein | |
| 2006/0074460 A1 | 4/2006 | Maghribi et al. | |
| 2007/0021841 A1 | 1/2007 | Al-Temen et al. | |
| 2007/0055383 A1 * | 3/2007 | King | 623/34 |

OTHER PUBLICATIONS

Andrews, A., E. Morin, and L. McLean, "Optimal Electrode Configurations for Finger Movement Classification using EMG," in Engineering in Medicine and Biology Society, 2009. EMBC 2009. Annual International Conference of the IEEE, 2009, pp. 2987-2990.
Choi, G. W., G. H. Choe, I. H. Moon, and M. S. Mun, "Development of Surface Myoelectric Sensor for Myoelectric Hand Prosthesis," in Power Electronics Specialists Conference, 2006. PESC'06.37th IEEE, 2006, pp. 1-5.
De Luca, C. J., R. S. Le Fever, and F. B. Stulen, "Pasteless Electrode for Clinical Use," Med. & Biol. Eng. & Comput, vol. 17, No. 3, May 1979, pp. 387-390.
Finni, T., M. Hu, P. Kettunen, T. Vilavuo, and S. Cheng, "Measurement of EMG Activity with Textile Electrodes Embedded into Clothing," Physiological Measurement, vol. 28, No. 11, Nov. 2007, pp. 1405-1419.

(Continued)

*Primary Examiner* — Linda Dvorak
*Assistant Examiner* — Brian M Antiskay
(74) *Attorney, Agent, or Firm* — Konrad Raynes Davda & Victor LLP; Alan S. Raynes

(57) ABSTRACT

An assembly may include a plurality of electrode contacts adapted to receive myoelectric signals from a body when placed into contact with the body. The assembly may also include a support structure adapted to support the electrode contacts. The assembly may also include a prosthetic liner, the support structure being embedded in the prosthetic liner. The electrode contacts may be positioned to be extending through openings in the prosthetic liner. The assembly may also include signal processing circuitry adapted to process the myoelectric signals from the body. Other embodiments are described and claimed.

17 Claims, 18 Drawing Sheets

(56) References Cited

OTHER PUBLICATIONS

Hargrove, L., K. Englehart, and B. Hudgins, "The Effect of Electrode Displacements on Pattern Recognition Based Myoelectric Control," Conf Proc IEEE Eng Med Biol Soc, vol. 1, 2006, pp. 2203-2206.

Hermens, H. J., B. Freriks, C. Disselhorst-Klug, and G. Rau, "Development of Recommendations for SEMG Sensors and Sensor Placement Procedures," Journal of Electromyography & Kinesiology, vol. 10, No. 5, pp. 361-374, Oct. 2000.

Lapatki, B. G., J. P. Van Dijk, I. E. Jonas, M. J. Zwarts, and D. F. Stegeman, "A Thin, Flexible Multielectrode Grid for High-Density Surface EMG," J. Appl. Physiol., vol. 96, No. 1, Jan. 2004, pp. 327-336.

Linz, T., Gourmelon, L., and Langereis, G., "Contactless EMG sensors embroidered onto textile," in 4th International Workshop on Wearable and Implantable Body Sensor Networks (BSN 2007), 2007, pp. 29-34.

Makino, Y., S. Ogawa, and H. Shinoda, "Flexible EMG Sensor Array for Haptic Interface," in SICE Annual Conference 2008, 2008, pp. 1468-1473.

Makino, Y., Ogawa, S., and Shinoda, H.,, "EMG Sensor Integration Based on Two-Dimensional Communication," in Networked Sensing Systems, 2008. INSS 2008. 5th International Conference on, 2008, pp. 140-147.

Makino, Y., Ogawa, S., and Shinoda, H., "EMG Sensor Array Integrated on a Flexible 2D Signal Transmission Sheet," Proc IEEJ 25th Sensor Symposium, 2008, pp. 671-674.

Makino, Y., Okada, A., and Shinoda, H., "Measuring Myoelectric Potential Patterns Based on Two-Dimensional Signal Transmission Technology," in SICE-ICASE, 2006. International Joint Conference, 2006, pp. 2005-2009.

Muhlsteff, J. and O. Such, "Dry Electrodes for Monitoring of Vital Signs in Functional Textiles," Conf Proc IEEE Eng Med Biol Soc, vol. 3, 2004, pp. 2212-2215.

Ochia, R. S. and P. R. Cavanagh, "Reliability of Surface EMG Measurements Over 12 Hours," Journal of Electromyography and Kinesiology, vol. 17, No. 3, Jun. 2007, pp. 365-371.

Roy, S., G. De Luca, M. Cheng, A. Johansson, L. Gilmore, and C. De Luca, "Electro-mechanical Stability of Surface EMG Sensors," Medical and Biological Engineering and Computing, vol. 45, No. 5, May 2007, pp. 447-457.

Taelman, J., T. Adriaensen, A. Spaepen, G. R. Langereis, L. Gourmelon, and S. Van Huffel, "Contactless EMG Sensors for Continuous Monitoring of Muscle Activity to Prevent Musculoskeletal Disorders," in Proc. of the first Annual Symposium of the IEEE/EMBS Benelux Chapter, 2006, pp. 223-226.

Tallgren, P., S. Vanhatalo, K. Kaila, and J. Voipio, "Evaluation of Commercially Available Electrodes and Gels for Recording of Slow EEG Potentials," Clinical Neurophysiology, vol. 116, No. 4, Apr. 2005, pp. 799-806.

Walbran, S. H., E. P. Calius, G. R. Dunlop, and I. A. Anderson, "A Technique for Optimizing Electrode Placement for Electromyographic Control of Prostheses," in Engineering in Medicine and Biology Society, 2009. EMBC 2009. Annual International Conference of the IEEE, 2009, pp. 1331-1334.

* cited by examiner

FIG. 7(a)
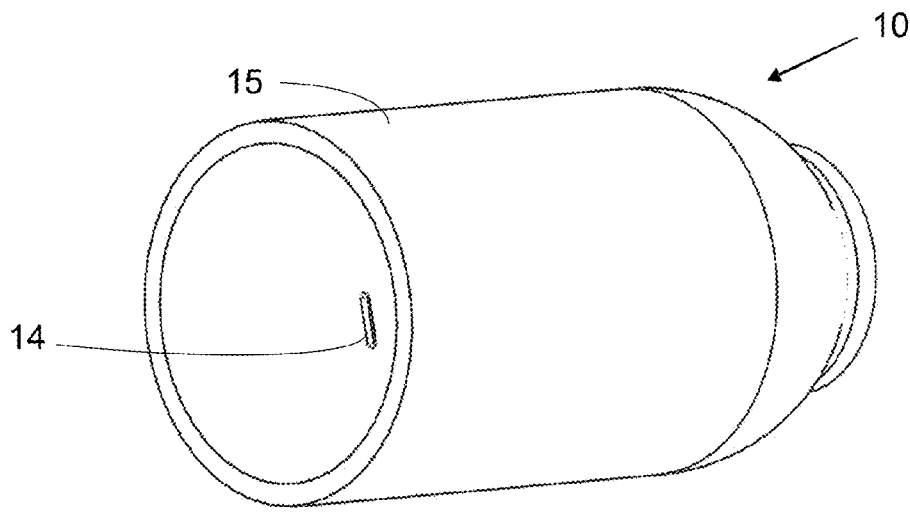
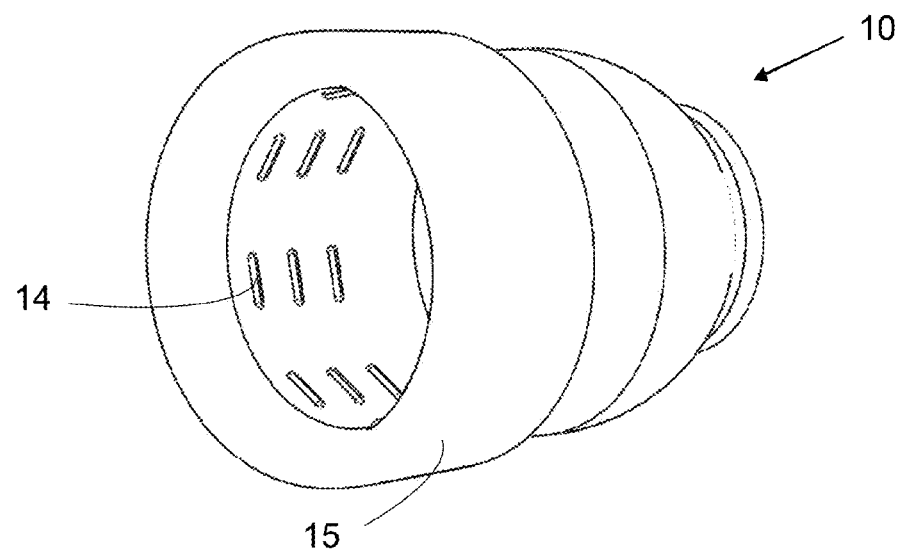
FIG. 7(b)

FIG. 10(a)
FIG. 10(b)
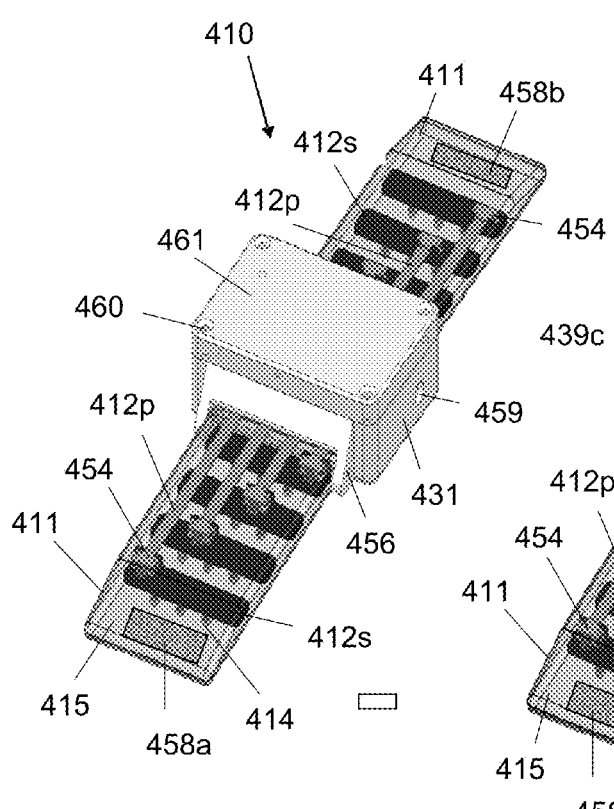
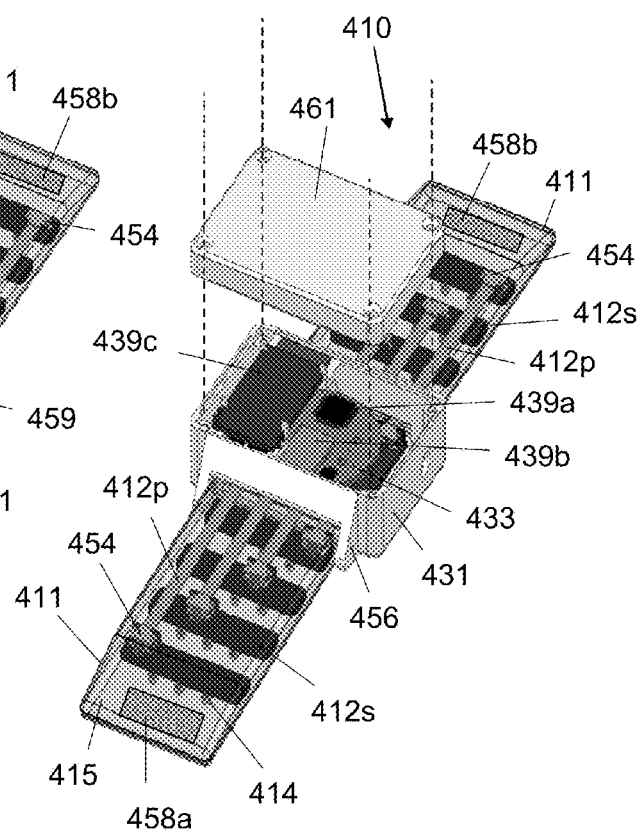

FIG. 15(a)
FIG. 15(b)
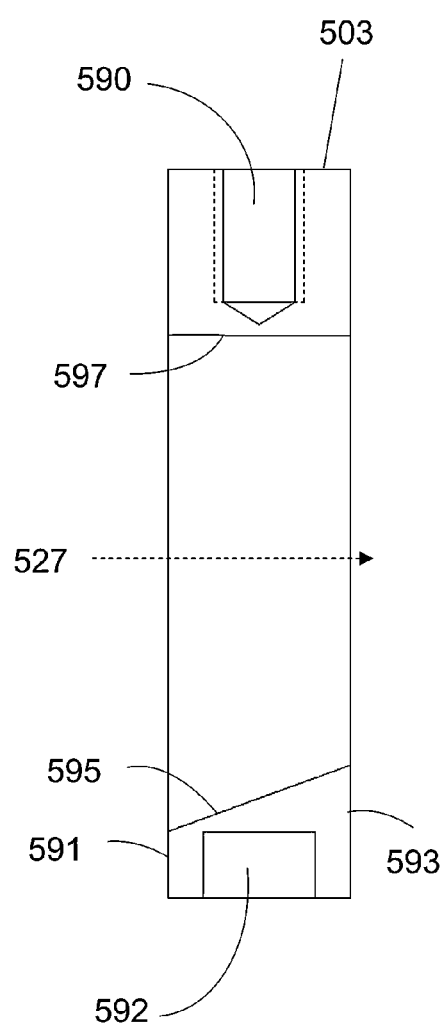
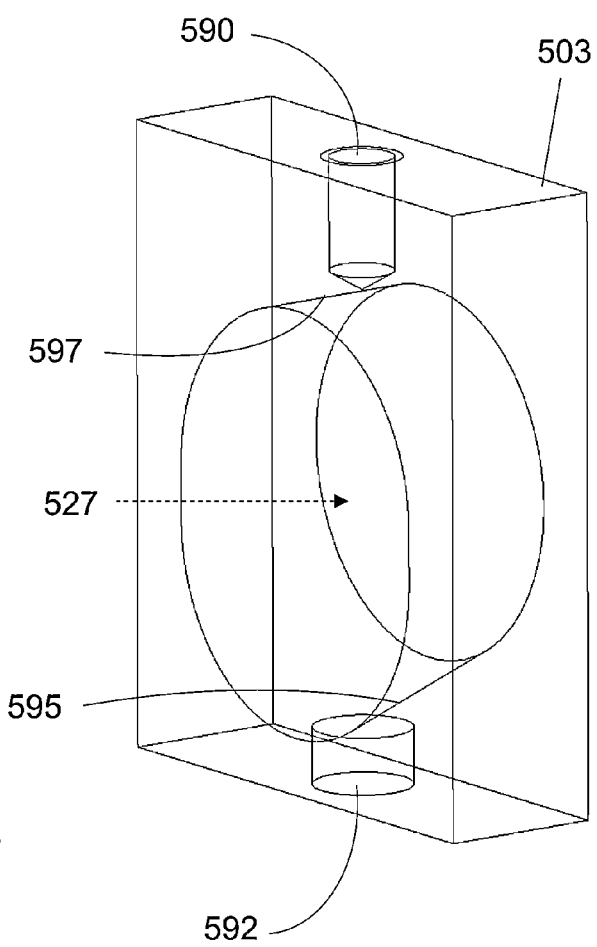

ELECTRODE ASSEMBLIES FOR DETECTING MUSCLE SIGNALS IN A PROSTHETIC LINER

RELATED ART

Muscles may generate electrical impulses known as myoelectric signals. Such myoelectric signals may be detected and amplified. An electrode interface may be used to extract myoelectric signals and communicate user intention. This electrode interface may be used in a prosthetic device to extract myoelectric signals from residual limbs of amputees and communicate intended movements to prosthetic devices.

Myoelectric prostheses are typically operated through the use of one or two surface electromyography (EMG) electrodes. These electrodes are placed over the belly of muscles on the residual limb or over other muscles more proximal to the site of amputation. The EMG signals are amplified, digitized and passed to a microcontroller which, in turn, operates a prosthetic limb such as a hand.

BRIEF DESCRIPTION OF THE DRAWINGS

FIG. 7a-7b illustrate an electrode assembly including an encasement, where a portion of the assembly may be rolled up, in accordance with certain embodiments.

FIGS. 10(a)-10(b) illustrates another band-like electrode assembly, in accordance with certain embodiments.

FIG. 14(a)-14(c) illustrates operations relating to a docking procedure including coupling a locking pin on an electrode assembly to a dock, in accordance with certain embodiments.

FIG. 15(a)-15(b) illustrate features of a latching mechanism used in an electromechanical dock, in accordance with certain embodiments.

Figure 1:
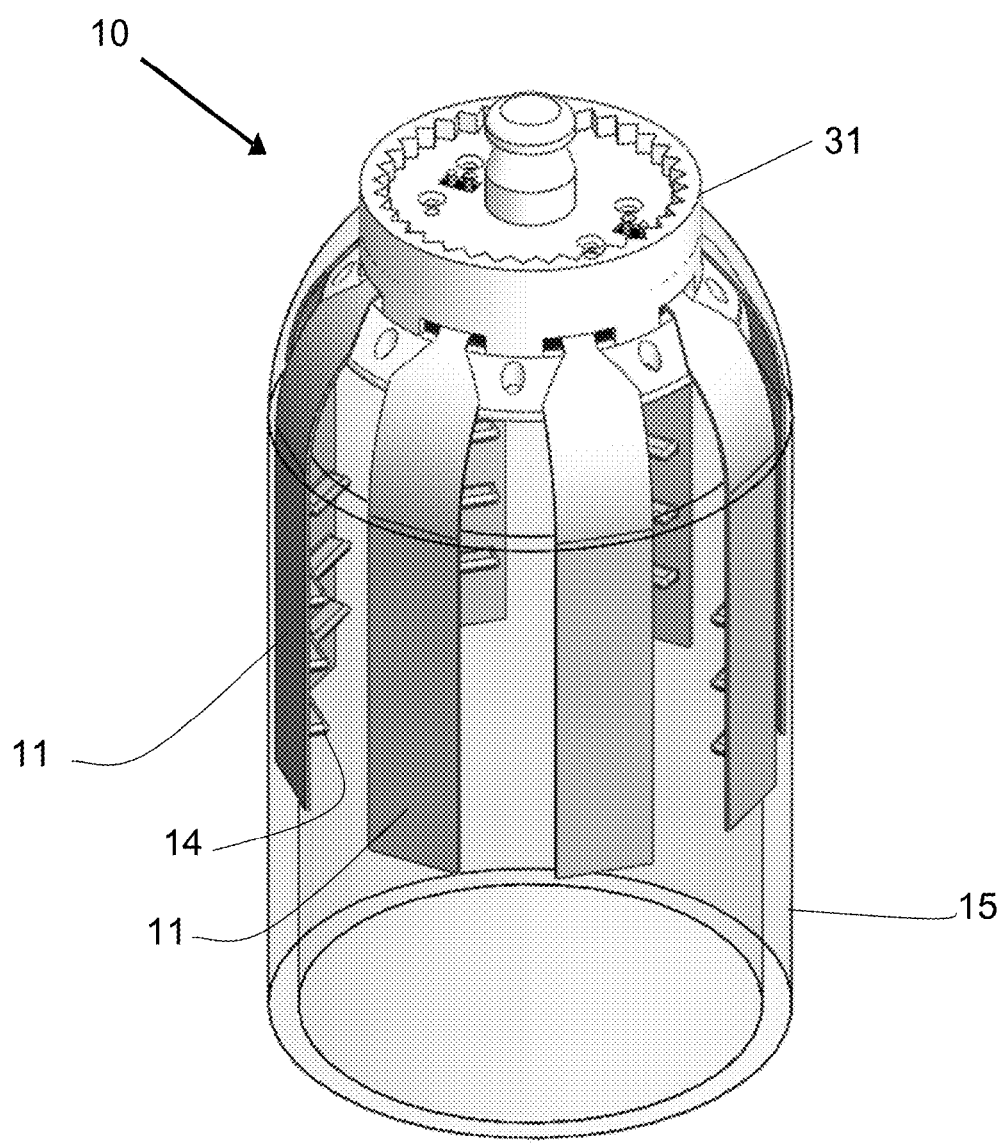
FIG. 1 illustrates an electrode assembly including eight legs, in accordance with certain embodiments.

The following description references the accompanying drawings, which represent various features in certain embodiments and are not necessarily drawn to scale. Specific features are numbered consistently across the multiple figures, with similar components in difference figures utilizing the same reference number.

DETAILED DESCRIPTION

The following description is set forth to enable one skilled in the art to make and use the invention. The descriptions of specific techniques, methods, and applications are used only as examples. Various modifications to these examples and descriptions would be apparent to one with skill in the art without departing from the scope of the invention. The scope of the invention is not limited to the embodiments represented.

Certain embodiments relate to methods and devices, including, but not necessarily limited to, those that relate to prosthetic limbs and components therein, including electrode assemblies that extract myoelectric signals and communicate intended user movements by using multiple electrodes.

In certain embodiments, an electrode assembly is comprised of one or more electrode contacts that are attached to legs that conduct the signal from the electrodes to a signal processing unit. One embodiment includes eight electrode legs attached to a central signal processing unit. The signal processing unit includes signal processing circuitry that can amplify and process myoelectric signals. Each electrode leg may include electrode contacts electrically coupled to an electrically conductive path. The conductive path may include, but is not limited to, a wire, a cable including one or more electrically conductive pathways, a layer deposited onto a substrate, and a printed circuit board. The electrode legs may be embedded within an encasement material, with openings in the encasement material for the electrodes to make contact with the skin of a device user.

A variety of materials may be used as an encasement material, including, but not limited to, silicones and thermoplastic elastomers. In certain embodiments, the electrode assembly including the encasement is configured to be in the form of a prosthetic liner that fits over a portion of a body such as a limb. Such a configuration may in certain embodiments be substantially cup-shaped, including a cup bottom and cup sides. In certain embodiments, the limb is positioned in the cup, with the signal processing unit located at the distal end (at the cup bottom) and the electrode legs radiating along the sides of limb (sides of the cup). The distal end of the assembly is the end closest to a receiving device; for example, an artificial hand The signals may be transmitted from the electrodes to the signal processing unit and from the signal processing unit to a receiving device. The receiving device may be any device where detecting user intention is necessary or desirable; an artificial hand being one example of a receiving device. The signal processing unit may include circuitry adapted to send a signal to control motion of one or more jointed structures on a prosthetic limb. A connection mechanism may be attached to the distal end of the assembly for connection with the receiving device. For example, if the assembly is a prosthetic liner that is worn over an amputees' residual arm, the connector may be coupled to an artificial hand. A docking mechanism may be used to couple the connector to the artificial hand. The connection mechanism may have different structural designs depending on the docking mechanism connection structure used.

While certain embodiments use eight electrodes, other embodiments may utilize a different number of electrodes, for example, two. Although certain embodiments use stainless steel electrode contacts, any type of electrode contact material may be used. These materials may include other metals and alloys, conductive polymers, conductive gels, conductive textiles, or other conductive materials. Other embodiments may have different placements of the signal processing unit. These embodiments may include placing the signal processing unit along the wall of the liner or include the use of separate signal processing units located directly on the electrode legs, near the electrode contacts.

Another embodiment enables extraction of myoelectric signals from the limbs of both able-bodied users and amputees using a different configuration. This embodiment includes an electrode assembly attached and extending outward from a central signal processing unit that can be worn by an individual in an arm band configuration. In this embodiment, the electrode assembly may include more than one electrode affixed to a flexible, conductive substrate.

Embodiments also relate to other components of a prosthetic limb, including, but not limited to, a docking mechanism used to couple the electrode assembly to a device such as a prosthetic hand.

Figure 2:
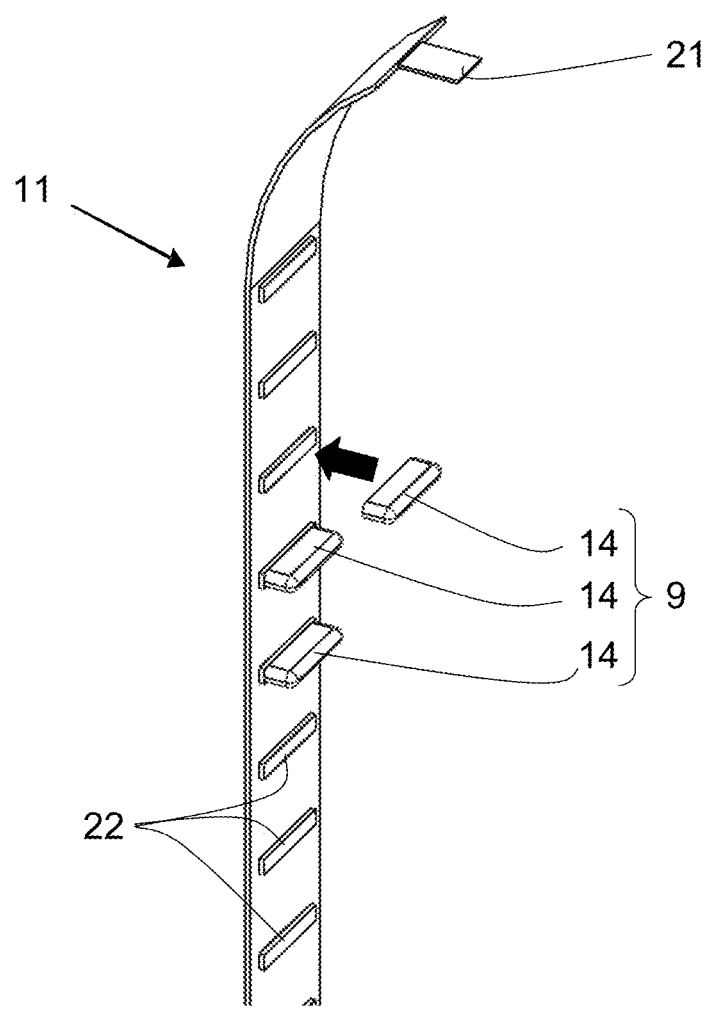
FIG. 2 illustrates certain features of a leg used in an electrode assembly, in accordance with certain embodiments.

Certain embodiments will be discussed in connection with the Figures. FIGS. 1-4 illustrate features in certain electrode assembly embodiments, including electrode legs 11 coupled to a signal processing unit 13 and encasement 15. FIG. 1 illustrates an embodiment of an electrode assembly 10 configured to fit over a user's residual limb. This embodiment uses a plurality of electrode contacts 14 coupled to a support structure taking the form of legs 11. As seen in FIG. 1, the assembly includes eight legs 11 that include electrodes positioned to contact a desired location on a user's body. The legs 11 have the electrode contacts 14 positioned thereon. FIG. 2 illustrates electrode contacts 14 that are coupled to a leg 11, in accordance with certain embodiments. In this embodiment, three electrode contacts comprise an electrode 9. The legs 11 may include one or more electrically conductive paths along which signals from the contacts 14 may pass. The electrically conductive paths may take a variety of forms, including, but not limited to, a body such as a wire, a cable, and a printed circuit board having electrically conductive traces. Where, for example, a wire or cable is used, the wire or cable may include a jacketed structure to ensure that short circuits between adjacent conductive paths do not occur and to protect the wire or cable.

FIG. 2 illustrates an embodiment in which the conductive path has a relatively flat shape, such as a flat wire or a flexible printed circuit board. In certain embodiments, the legs 11 may be formed to have sufficient strength and mass to support the contacts 14 while at the same time being somewhat flexible. Depending on the number of contacts alone each leg 11, a plurality of electrical paths may be utilized along each leg 11. Thus, in an embodiment having three electrode contacts 14 in a single leg 11 may include no less than three electrically conductive paths (insulated from each other) to transmit the signals from the three contacts 14. Other embodiments may include an electrode having a different number of electrode contacts 14. The electrode contacts 14 may comprise any conductive material, including, but not limited to, stainless steel, and the contacts may take a variety of shapes, including, but not limited to, a bar contact as illustrated in FIG. 2. The electrical activity detected by the electrode contacts 14 of the electrode 9 may be transmitted through the electrode leg to the signal processing unit 13 via a terminal such as terminal 21. In certain embodiments, electrode contacts 14 can be placed at various attachment areas 22 down the length of the legs 11 to accommodate users including amputees with various residual limb lengths. This arrangement allows for customization in the placement of the electrodes.

The signals from the electrode contacts 14 are transmitted to signal processing circuitry in a signal processing unit 13 (see FIG. 3) positioned in a central region of the electrode assembly 10. An end of the leg 11 may be formed with terminal 21 that is coupled to connector 34 in the signal processing unit 13. The signal processing unit 13 includes signal processing circuitry and may also include one or more other structures including, but not limited to, a board onto which the circuitry is attached, connectors for attaching electrode legs, a base, a housing, and hardware to attach the components to the assembly, as described in connection with FIG. 3. Each of the legs 11 may be electrically coupled to the signal processing unit 13.

In addition, the legs 11 may be embedded within an encasement 15, which may be formed from, for example, a flexible material such as, for example, a silicone or thermoplastic elastomers. In certain embodiments, at least a portion of the signal processing unit 13 may also be embedded in the encasement 15. For example, the portion of the assembly at the level where the legs 11 are attached to the connectors 34 of FIG. 3 may be embedded within the encasement 15. In other embodiments, the signal processing unit 13 is not embedded in the encasement 15. The encasement 15 may range from transparent to opaque in appearance, depending on its composition. As illustrated in FIG. 1, for example, the signal processing unit 13 may in certain embodiments be located at the closed end of the assembly (opposite the opening through which a user's limb may be positioned). The overall shape of the electrode assembly in the embodiment illustrated in FIG. 1 is substantially cup-shaped, including a cup bottom and cup sides, with the central region being positioned at the cup bottom and the electrode support legs being positioned to extend up the cup sides. As illustrated in FIG. 1, the cup is upside down.

In certain embodiments, the electrode contacts 14 may be coupled to the legs 11 with a conductive adhesive. Other suitable connection mechanisms including, but not limited to, soldering, welding, and crimping, may also be used. Even though the embodiment illustrated in FIG. 2 uses an electrode 9 including three metal electrode contacts 14 in a double-differential configuration, monopolar or bipolar metallic or non-metallic electrode configurations may be used. Any type of surface electrodes may be used in any shape or attachment configuration. In one embodiment, the leg 11 comprises a flat cable having an insulating jacket, the cable including three electrically conductive paths, and the electrodes 9 include contacts 14 that are crimped into contact with the cable, with each contact 14 being placed into electrical contact with a separate conductive path.

Figure 3:
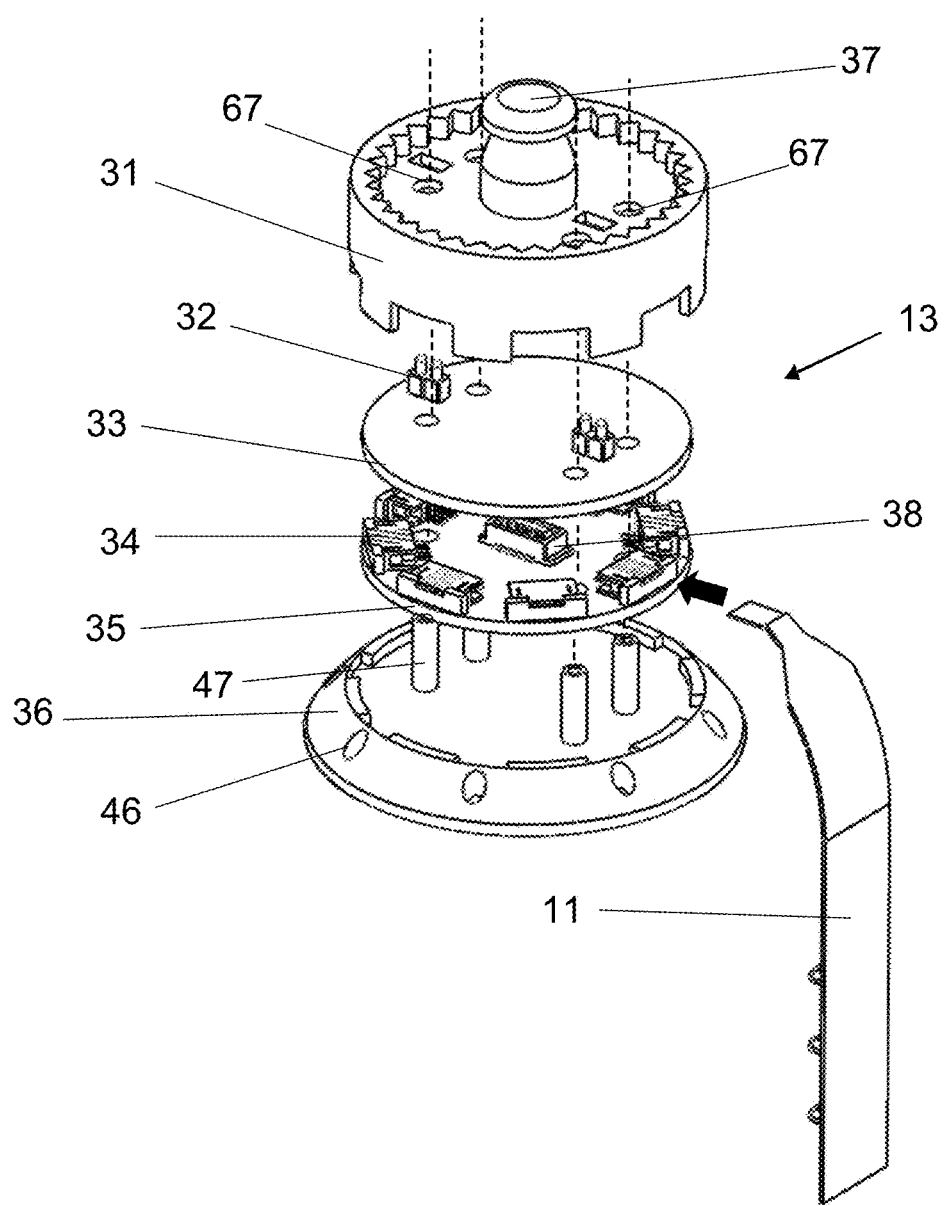
FIG. 3 illustrates details of a signal processing unit and mechanical connection mechanism, in accordance with certain embodiments.

FIG. 3 illustrates an expanded view of certain features of an assembly including the signal processing unit 13 in accordance with certain embodiments. The signal processing unit 13 may include signal processing circuitry 39 that is in certain embodiments coupled to a body such as, for example, a printed circuit board 33. The signal processing unit 13 printed circuit board 33 ("processing PCB 33") may in certain embodiments be positioned in a central region of the assembly. In certain embodiments, the signal processing circuitry may be positioned on a bottom surface of the processing PCB 33 illustrated in FIG. 3. The PCB 33 may be coupled within the assembly in such a manner so that it is easily detachable. That way, if, for example, one or more components in the circuitry fail, or if updated circuitry is desired, the PCB 33 may be easily replaced.

Figure 4:
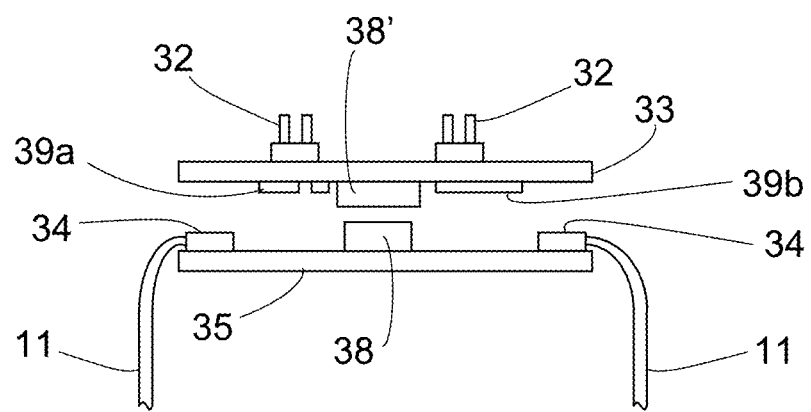
FIG. 4 illustrates a portion of an electrode assembly including signal processing circuitry and legs coupled to connectors, in accordance with certain embodiments.

FIG. 4 illustrates a cross sectional view of portions of an assembly in accordance with certain embodiments, including signal processing circuitry 39a, 39b positioned on a bottom surface of the processing PCB 33. The signal processing unit 13 may perform a number of different processing functions on the signal from the electrode contacts 14 once the signal is received. Placing the processing PCB 33 relatively close to the electrode contacts 14 reduces the noise picked up along the conduction path between the contacts 14 and signal processing hardware to produce a clearer signal. In certain embodiments, electrode legs 11 are attached to, for example, low-profile connectors 34 located on a structure in the central region of the assembly. The structure to which the connectors 34 are coupled may, for example, be a junction printed circuit board 35 ("junction PCB 35"), which is then connected to the processing PCB 33. The processing PCB 33 and junction PCB 35 may be electrically connected using any suitable mechanism, for example, board-to-board connectors. Male or female board-to-board connectors 38 are connected to circuitry of the junction PCB 35 and the opposite gender board-to-board connectors 38' are connected to the circuitry of the processing PCB 33. FIGS. 3 and 4 show one board-to-board connector 38 and opposite gender board-to-board connector 38', but additional board-to-board connectors may be used if necessary.

In certain embodiments, the signal circuitry 39a, 39b and the electrode connectors 34 may be positioned on the same structure, for example, a single PCB. In one such embodiment, the processing circuitry 39a, 39b could be placed onto the junction PCB 35. In such an embodiment, board-to-board connectors are not necessary.

Signals may be sent from, for example, a microprocessor/controller of the signal processing circuitry 39a, 39b of the signal processing unit 13 using a variety of suitable methods, including, but not limited to, wireless Bluetooth™ technology, electric wires, or conductive connectors such as, for example, spring-loaded conductive pins 32. Spring-loaded pins 32 on the top side of the processing PCB 33 as illustrated in FIG. 3 conductive circuitry will transmit the appropriate signals to the appropriate receiving device, which in certain embodiments will be a prosthetic device such as a hand. The signal processing unit 13 may further include housing 31 and base 36. A locking pin 37 may extend outward on the top portion of the housing 31 to couple to the receiving device (for example, a prosthetic hand) or to an intermediate structure that in turn is coupled to the receiving device. The type of connector used to send the signals may depend on the type of receiving device. The housing 31 may also include base 36 made of metal, plastic, or any suitable material, with certain embodiments utilizing components made of a lightweight, durable plastic such as Delrin™ that is non-conductive. The base 36 may include one or more anchor holes 46. As illustrated in FIG. 1, embodiments may include an encasement 15 and the material of the encasement 15 may flow into the anchor holes 46 to ensure that the signal processing unit is strongly anchored to the encasement 15. Various components of the assembly may be positioned using mounting posts 47. As illustrated in FIG. 3, the mounting posts 47 are used to support and align the junction PCB 35, the processing PCB 33, and the housing 31. Apertures 67 may extend through the junction PCB 35, the processing PCB 33, and the housing 31 to facilitate the positioning and attachment of the components using the mounting posts 47. The mounting posts 47 may be internally threaded so that mounting screws (not shown) may be used to couple the upper and lower components to the mounting posts 47.

The shape of housing and signal processing unit is shown to be generally cylindrical in FIG. 3, but it could be any three-dimensional shape. The electrode legs 11 may have a variety of shapes. For example, as illustrated in FIG. 3, the electrode leg 11 may be tapered near its upper end in order to facilitate its connection to the connectors 34. In certain embodiments, the electrode legs 11 are positioned at equally spaced intervals.

Figure 5:
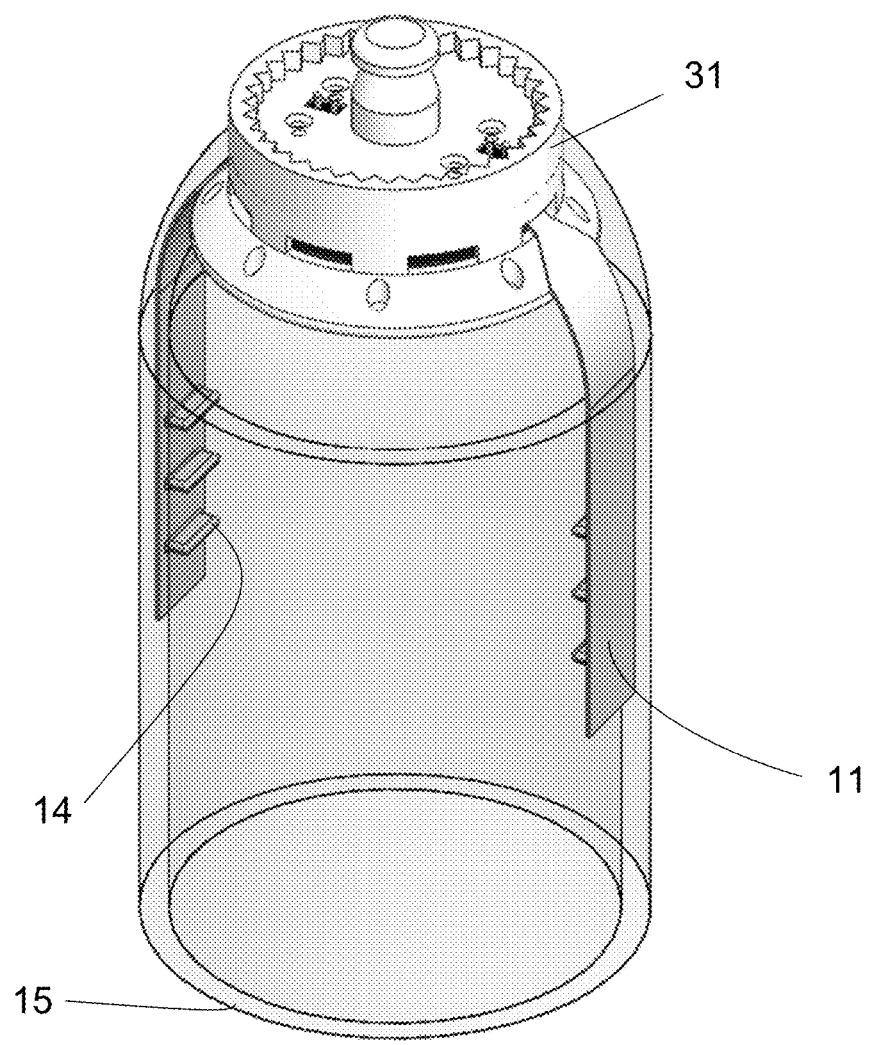
FIG. 5 illustrates an electrode assembly which uses two legs, in accordance with certain embodiments.

FIG. 5 illustrates an embodiment of an electrode assembly that is similar to that illustrated in FIG. 1 and described above, except that this embodiment includes two legs 11. Even though other embodiments use eight electrode legs, embodiments may include a different number of electrode legs, with certain preferred embodiments utilizing any number from two to eight electrode legs. Certain embodiments may include multiple legs and electrodes evenly spaced apart, whereas in other embodiment the legs and/or electrodes may be unevenly spaced apart. The spacing may depend on the condition of the user's appendage over which the assembly is positioned. One specific embodiment utilizes three electrode legs evenly spaced apart. Certain embodiments also permit the positioning of more than one electrode on an electrode leg. Embodiments also permit the use of more than eight electrodes and more than 8 electrode legs, if desired.

Figure 6:
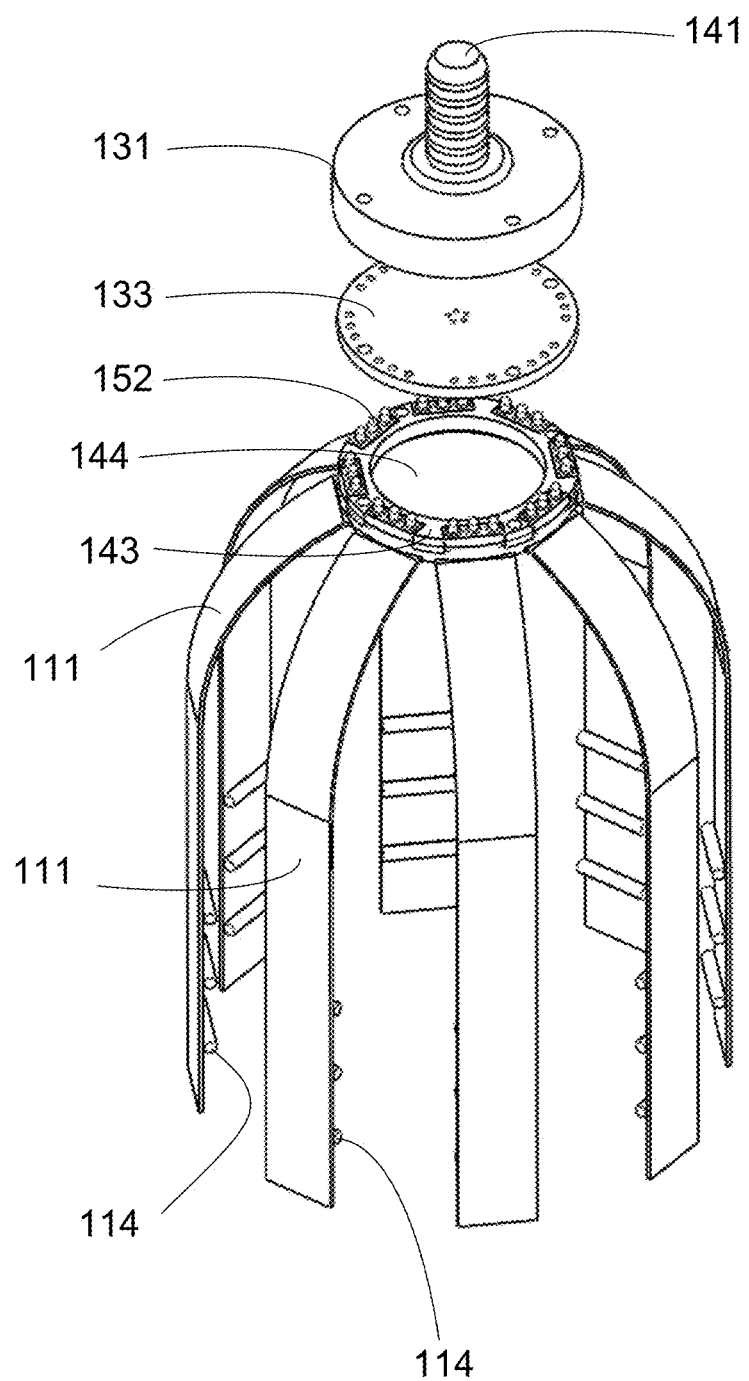
FIG. 6 illustrates an electrode assembly utilizing integrated legs, in accordance with certain embodiments.

FIG. 6 illustrates an embodiment of an electrode assembly having integrally formed electrode legs. The legs 111 are similar to the legs 11 illustrated in FIGS. 1-5, however, they are all formed as part of the same body. This embodiment uses a support structure such as, for example, a flexible PCB material comprising eight legs 111 having contacts 114 mounted thereon to conduct signals to the signal processing circuitry. The signal processing circuitry may be placed on, for example, a detachable printed circuit board ("processing PCB") 133, which may be similar to the processing PCB 33 described earlier. The support structure in this embodiment is in the shape of a starburst with eight rays (legs 111) radiating outward and downward from a central region 144, as illustrated in FIG. 6. The eight legs 111 illustrated in FIG. 6 differ from the legs 11 (of FIG. 3, for example) because the legs 111 in FIG. 6 are formed to be integral with each other. In other words, the support structure in FIG. 6 is a one-piece structure having eight rays that act as the legs 111 and a central portion 144 from which the legs 111 extend.

In certain embodiments, such as the embodiment illustrated in FIG. 6, the signal processing circuitry of the signal processing unit 113 may be placed on or above the central portion 144, instead of being placed onto another board. In other words, in certain embodiments, the processing PCB may be omitted and the circuitry mounted on an underlying surface. As illustrated in FIG. 6, such an embodiment would omit processing PCB 133 and mount circuitry on the portion 144. In other words, part of the support structure (in this embodiment, the portion 144) may act as a processing PCB. However, such a configuration may not permit the easy detachability of the signal processing circuitry from the assembly, which, as noted above, may in certain situations be desirable.

In the embodiment illustrated in FIG. 6, the processing PCB 133 may be joined to the support structure using spring-loaded terminals 152. The spring-loaded terminals 152 allow for the conduction of the signal from the electrical paths on the legs 111 of the support structure to the processing PCB 133. In such an embodiment, one end of the spring-loaded terminals 152 may be embedded on a mounting bracket 143. The other end of the spring loaded terminals 152 may be in contact with the circuitry of the processing PCB 133. The signals may be sent from the microprocessor/controller of the signal processing unit 13 using wireless communication, electric wires, or conductive connectors such as a coaxial conductive connector 141. The type of connector used to send the signals may depend on the type of receiving device. Where the receiving device has a female end of a coaxial connector, then a coaxial connector 141 would likely be a preferable selection. A variety of connectors may be used depending on the receiving device. In this embodiment, housing 131 made of metal, plastic, or other materials may be attached to the top of the processing PCB 133 and act to protect the circuitry and provide cosmetic appeal. The housing 131 in this embodiment may have an aperture to allow the coaxial connector 141 to protrude from the distal end of the assembly. Though not illustrated in FIG. 6, an encasement similar to the encasement 15 of FIG. 1 may also be present in the assembly.

Certain embodiments use silicone or a thermoplastic elastomer as the material for the encasement 15, but other materials including, but not limited to, other flexible polymeric and/or rubbery materials, may be used. The adhesive properties of silicone rubber on skin tend to improve the signal quality during motion because the electrode contacts will tend to stay in place. In certain embodiments an electrode assembly including an encasement is formed to be of sufficient flexibility so that it can be rolled up and then placed over a limb (or portion of a limb) and then unrolled over the limb. For example, as illustrated in FIGS. 7(*a*)-7(*b*), an electrode assembly 10 having encasement 15 may be formed so that a portion of the encasement 15 (and legs) is rolled up as illustrated in FIG. 7(*b*). In an embodiment in which the electrode assembly has a cup-like shape when in placed on a limb, the electrode legs and encasement making up the sides of the cup are rolled up (or down depending on the orientation) towards the distal end of the assembly (bottom of the cup). The rolled up electrode legs and encasement may be unrolled over the limb to provide a secure fit thereon. For example, if the assembly 10 of FIG. 7 (*a*) is to be positioned over an amputee user's relatively long residual limb, then by rolling up a portion of the assembly 10, it may be easier to position the electrode contacts 14 onto positions near the end of the user's limb, and then roll down the portion of the encasement 15 to securely position the assembly 10 on the user's limb.

It should be appreciated that conventional prosthetic devices are limited to articulating one or two movements due to the limited source of information recorded from two surface electromyography (EMG) electrodes. In order to better ascertain the user's intention, an array of more than two electrodes, as in certain embodiments described herein, may be used to garner more information from muscles in the body and thus permit more sophisticated movements to be carried out by a prosthetic device such as, for example, a hand.

Embodiments may use a signal processing unit having a shape other than a cylindrical shape. Other shapes for the signal processing unit may include, but are not limited to, cubes, spheres, hemispheres, and pyramids. The central region may also have a variety of shapes, including, but not limited to, a square, a rectangle, a circle, and an octagon. The electrical path used to conduct the signals from the electrodes to the signal processing unit may be made using wires or cables, a PCB (flexible or inflexible) or other suitable materials. Wireless transmission may also be used in certain embodiments to transmit the signals from the electrodes to the signal processing unit and for transmitting other signals to and from the electrode assembly. Also, certain embodiments place the electrode connectors on a board positioned below the board containing the signal processing circuitry, for example, as illustrated in FIG. 3. Other embodiments may place the electrode connectors and signal processing unit on the same surface, depending on the purpose and environment of the electrode assembly. Further, as illustrated in various embodiments, a prosthetic electrode assembly may have the signal processing unit at the closed end of the liner with the electrode legs extending radially away from the central unit and down the side of the liner. In other embodiments, the electrodes and one or more signal processing units may be placed in other arrangements. The placement of the electrodes and the signal processing unit may be determined by the particular use of the electrode assembly.

Figure 8:
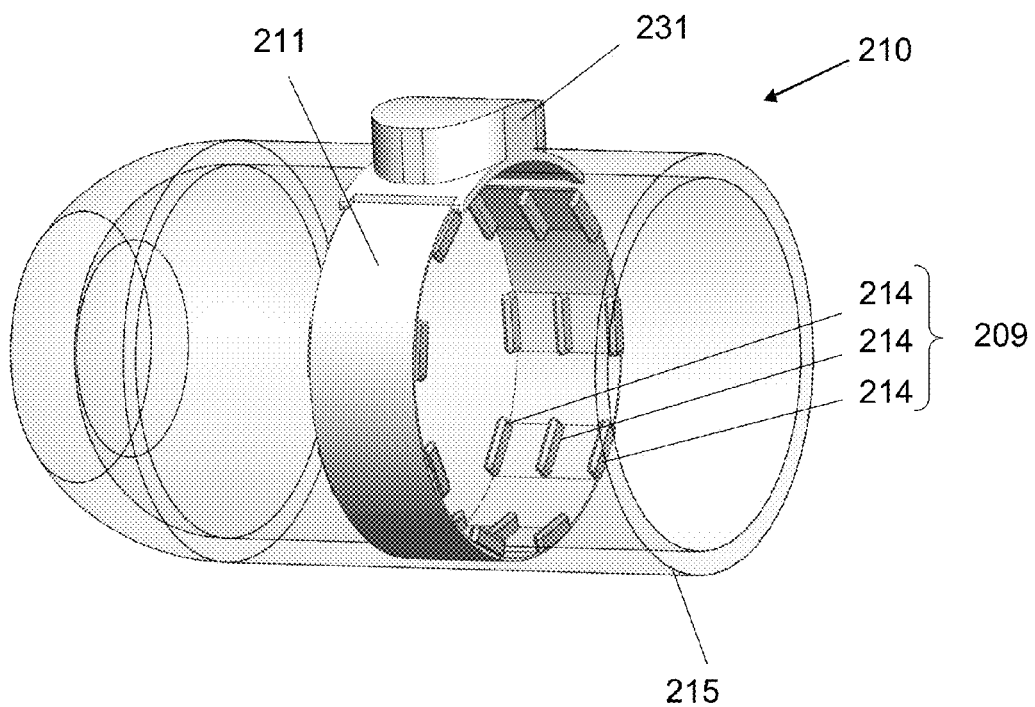
FIG. 8 illustrates an electrode assembly configured to includes an electrode support structure that extend circumferentially around a limb, in accordance with certain embodiments.

For example, a signal processing unit or units may be placed along a sidewall of the assembly and one or more electrode legs may extend laterally in a circular manner around all or most of the assembly, in a band-like configuration. Such an embodiment may maintain the cup shaped closed end but include one or more band-like electrode supports that extend around or nearly around a user's limb circumferentially. Such an embodiment would be preferred in applications where, for example, space is limited at the distal end of the assembly. FIG. 8 illustrates such an embodiment, including a band-like electrode support 211 such as a flexible PCB or other material having a suitable pathway for the transmission of signals from the electrode contacts. The support structure, as illustrated in FIG. 8, may be embedded in an encasement 215, and may take the form of a band 211. The band 211 and encasement 215 may be formed from the same materials as indicated above for the legs 11 and encasement 15. The band 211 may be similar to a leg 11 such as illustrated in FIG. 1 except that the band 211 is configured to extend around a user's limb circumferentially. Electrode contacts 214 are positioned on the band 211. In this embodiment, three electrode contacts 214 make up an electrode 209, and eight electrodes 209 are positioned on the band 211. The electrode 209 and contacts 214 may be formed from the same materials as indicated above for electrode 9 and contacts 14. A signal processing unit similar to the unit 13 of FIG. 3 may be position within housing 231 on a side of the assembly 210, so that the signal processing circuitry is positioned as close to the electrodes 209 as possible. The housing 231 may be formed from the same material as indicated above for housing 31. The shape of the housing 231 may be somewhat modified from that of housing 31, due to the different shape of the underlying surface. In addition, the housing may include a portion configured to accept part of the band 211.

As noted above, certain embodiments may utilize an electrode assembly having a band-like configuration. Another example of an embodiment having a band-like configuration includes a multi-electrode arm band interface assembly that does not have a cup-like shape. The arm band assembly provides a way to extract myoelectric signals from ablebodied users as well as the residual limbs of amputees. The arm band may include an encasement and at least two electrodes, a signal processing unit, and circuitry that conducts the signals from the electrodes to the signal processing unit in a band-like configuration.

Figure 9:
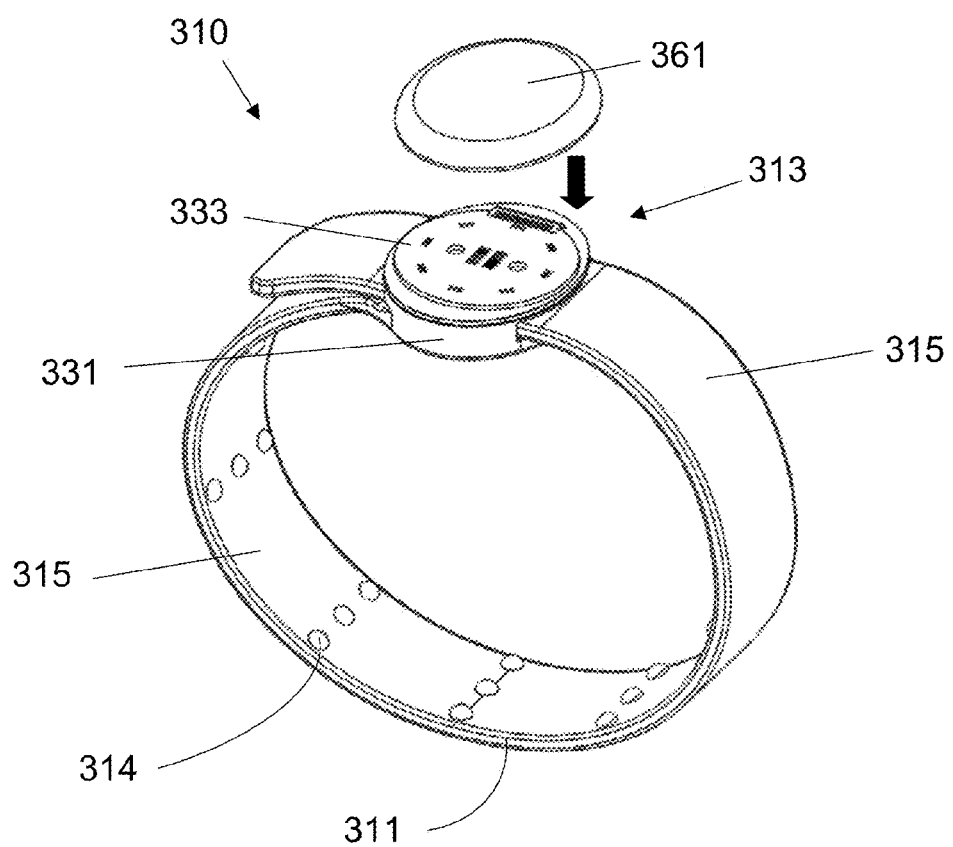
FIG. 9 illustrates an electrode assembly in a configuration that may be used as an arm band, in accordance with certain embodiments.

FIG. 9 illustrates one embodiment of an electrode assembly that may be configured as an arm band. This assembly 310 may use a signal processing unit 313 that is similar to the unit 13 described above, including signal processing circuitry (such as circuitry 39 illustrated in FIG. 4) coupled to a circuit board 333 such as, for example, a detachable printed circuit board ("processing PCB"). The arm band assembly 310 may include a number of electrode contacts 314 coupled to a support that includes suitable electrically conductive pathways, in the form of a band 311. The band 311 may be formed from a flexible material to ensure the best fit of the assembly over a user's appendage. Certain embodiments may include a band 311 including up to eight electrodes each having half-round contacts. The band 311 may include a material such as a flexible PCB, flat cable, or other support structure and including a suitable electrical pathway or pathways to transmit the signals from the electrode contacts 314 to the signal processing unit 313. The band 311 may be coupled to the processing unit housing 331 and can be wrapped around a limb much like a wrist watch having a single band that extends around the limb, with the housing 331 including a suitable connection mechanism to connect the band 311 thereto. The band 311 and contacts 314 may in some ways be similar to an electrode leg 11 as illustrated in other Figures and described above, with one difference being that the band 311 is configured to extend around a user's appendage. The band 311 may also include multiple electrodes with multiple contacts 314. While half-round electrode contacts 314 are illustrated, other shapes may also be used. The assembly may be partially or fully encased in an encasement material such as, for example, silicone, rubber, or a thermoplastic elastomer (with openings for the contacts 314) to provide comfort and flexibility. For example, the inner facing surface and the outer facing surface on the band 311 may include encasement 315 formed from the same material as encasement 15 described above. The signal processing unit 313 may transmit the necessary signals to a receiving device (not shown in FIG. 9) via wired or wireless link. The receiving device can be any device capable of being controlled by the signal processing unit. A plastic cover 361 may be positioned over the circuit board 333 to protect the internal electronics.

Another embodiment having a band-like configuration is illustrated in FIGS. 10(a)-10(b). The assembly 410 includes a two piece band configuration that is similar in configuration to a wristwatch utilizing a two piece band. As illustrated in FIG. 10(a), the assembly 410 includes two band portions 411 that are coupled to a signal processing unit having a housing 431 that houses signal processing circuitry therein. The band portions 411 may each be pivotally coupled to the housing 431 using a pin 456 extending therethrough at one end region, with the pin 456 also extending into an aperture in the housing 431 in a manner similar to that of a two piece watch band. The other end region of one or both of the band portions 411 may include a suitable connection mechanism 458a, 458b, including, but not limited to, a clasp or Velcro™. The connection mechanism enables the band-like sections to be coupled together to close around an appendage, in certain embodiments, for example, like a watch band. Each of the band portions 411 includes a plurality of electrodes including electrode contacts 414. As illustrated, three electrode contacts 414 are positioned on a support 412s. The support 412s is electrically coupled to an electrically conductive pathway 412p using connector 454. The electrically conductive pathway 412p extends towards the housing 431 and is electrically coupled to the signal processing circuitry therein. As illustrated in FIGS. 10(a) and 10(b), each of the band portions 411 includes four supports 412s and three electrode contacts 414 positioned on each of the supports 412s. A cover 461 is positioned on the housing 431. Threaded apertures 460 may be formed to enable the cover to be coupled to the housing 431 using screws (not shown). An aperture 459 may be positioned on a side of the housing 431 to enable control of one or more components inside the housing.

FIG. 10(b) illustrates the assembly of FIG. 10(a) with the cover 461 removed. The signal processing circuitry 439a, 439b, and 439c may be positioned within the housing 431. Some or all of the circuitry may be positioned on a board 433, such as a detachable printed circuit board. The assembly may also include an encasement 415 that covers the band portions 411. The encasement 415 may be formed from a variety of materials such as described above for encasement 15, for example, a silicone or thermoplastic elastomers. The encasement may be formed to provide openings so that the electrode contacts 414 can be in contact with a user's skin. The encasement 415 may be formed so that the band portions 411 are embedded therein.

As was described when describing the electrode assembly, the signal processing unit of the multi-electrode arm band assembly may perform a variety of processing functions on the signals once the signals are received. Placing the signal processing circuitry as close as possible to the electrode contacts allows for the conduction of clearer signals. In addition, it should be noted that am assembly described as an arm band may be used over a leg or other portion of a body.

The signal processing unit of the various embodiments may multiple devices such as analog to digital converters, amplifiers, controllers/microprocessors, resistors, and capacitors. The signal processing unit may contain more or less processing devices depending on the desired purpose of the electrode assembly. An analog to digital convertor may be used to convert the analog signals received from the electrodes into digital signals. An amplifier may be used to increase the amplitude of the digital signals. Resistors and capacitors may be used to control and direct the signals. A microprocessor/controller may be used to send the signals to the receiving device via Bluetooth™ or a conductive connector; for example, to a receiving device such as an appendage, as discussed above, or to another type of device including, but not limited to, a video game system or personal computer (PC). The signal processing unit may also include components such as accelerometers, gyroscopes, and/or other devices which can be used to provide motion tracking information may be used to track the position of the limb in space. For example, in certain embodiments, the motion tracking information may be used to position a cursor on a television, gaming, or PC screen.

Figures 11A, 11B, 11C, 11D:
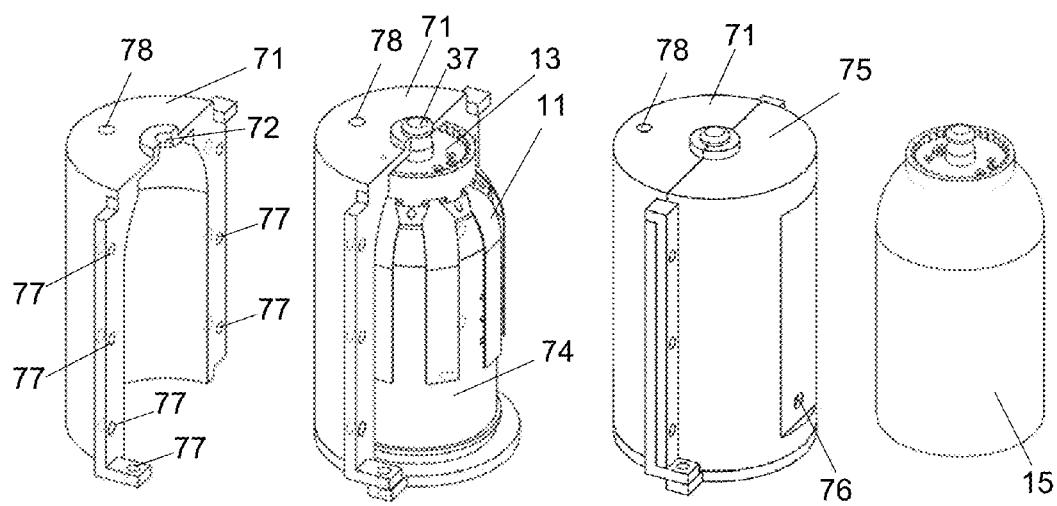
FIGS. 11(a)-11(d) illustrate operations in a molding process used to fabricate a an electrode assembly including an encasement, in accordance with certain embodiments.

Embodiments also relate to method for manufacturing electrode assembly structures. FIGS. 11a to 11d illustrate one example of a molding process that may be used to fabricate an electrode assembly in accordance with certain embodiments. The fabrication process includes four primary operations. In FIG. 11a, a negative mold 71 with similar dimensions to a patient's residual limb will be selected. In FIG. 11b, a partial electrode assembly, including the electrode legs 11 and signal processing unit 13 will be attached to a positive mold 74, which will have pre-designed crevices, corresponding to desired electrode locations. A housing connector (such as locking pin 37) may be secured within a cap lock 72 of one side of the negative mold 73. In FIG. 11c, both portions of the negative mold 71, 75 are secured in place (through screw holes 77 around the positive mold having the electrodes and signal processing unit assembly 73 thereon, and the entire mold structure is sealed to prevent leakage. The silicone is injected into the mold at the injection port 76 and allowed to cure, creating the encasement 15 illustrated in FIG. 1. Exhaust port 78 may also be present in the mold to vent gases or silicone overflow. In FIG. 11d, the assembly is removed by carefully pulling away the electrode legs 11 and signal processing unit 13 from the crevices in the positive mold 74. The electrode legs are encased in the encasement material (for example, silicone rubber), while the electrode contacts are exposed to be able to touch the skin of the user.

Figure 12A:
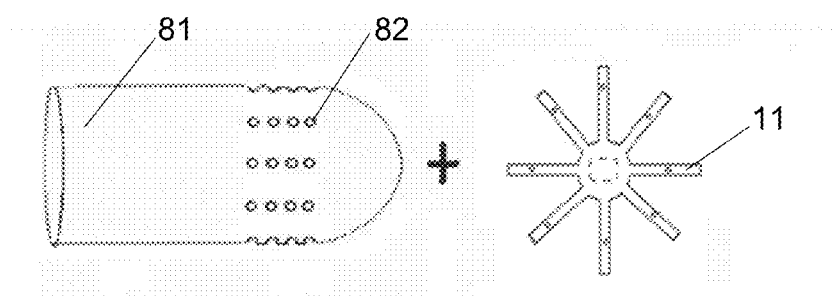
FIGS. 12(a)-12(c) illustrate the formation of an electrode assembly including an encasement having inner and outer encasement layers, in accordance with certain embodiments.
Figure 12B:
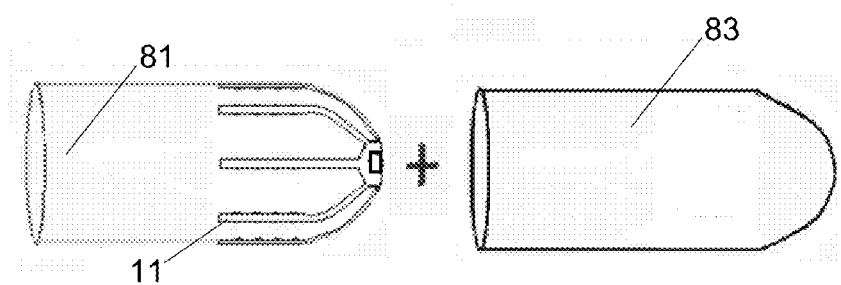
Figure 12C:
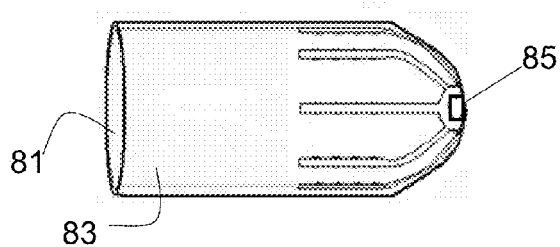

Another embodiment may include separate inner and outer encasement layers. Such layers may be formed using a molding process in some ways similar to that described above, to form an inner layer and an outer layer, as illustrated in FIGS. 12a-12c. FIG. 12a illustrates the legs 11 and an inner encasement layer 81. The inner encasement layer 81 may include a plurality of apertures 82 through which the electrode contacts on the legs 11 may extend. FIG. 12b illustrates the legs 11 positioned on the inner encasement layer 81, and an outer encasement layer. A plurality of the apertures 82 are formed along the length of the inner encasement layer so that the electrode contacts 14 may be located at varying positions. FIG. 12b also illustrates the outer encasement layer 83 sized to fit over the inner encasement layer 81 and the legs 11. FIG. 12c illustrates the outer encasement layer positioned over the inner encasement layer 83 and the legs 11. The encasement layers 81 and 83 may act to sandwich the legs 11 in place. Signal processing circuitry may in certain embodiments be positioned at or near a distal end 85 of the assembly. In various embodiments, electrodes may be located at the appropriate recording sites specific to a given amputee. The electrodes will protrude from the inner surface of the encasement layer to maintain good contact with the skin. In certain embodiments, the electrode legs will terminate at or near the signal processing unit.

Certain embodiments may utilize a connection mechanism such as a connector or locking pin to mechanically and/or electrically couple the electrode assembly to a receiving device. The receiving device may be a prosthetic hand or a docking mechanism coupled to the prosthetic hand. For example, FIG. 5 illustrates a connector 41 that is a coaxial connector that acts to transmit electrical signals from the electrode assembly to a device such as a docking mechanism. Alternatively, FIG. 3 illustrates a locking pin 37 that is used to form a mechanical connection between the electrode assembly to a docking mechanism. In the embodiment illustrated in FIG. 3, spring-loaded pins 32 may be used to make the electrical connection from the electrode assembly to the device such as a docking mechanism.

As noted above and illustrated, for example, in FIG. 3, a locking pin 37 may be used to couple the electrode assembly to a docking mechanism for a receiving device (for example, a prosthetic hand). The locking pin 37 may be attached to the distal end of the electrode assembly for connection with the docking mechanism. The docking mechanism may in certain embodiments act to both mechanically and electrically couple the electrode assembly to the receiving device. The docking mechanism also ensures that the prosthetic liner is properly mechanically coupled to the remainder of the prosthesis. The structure of the connection mechanism and the docking mechanism may vary depending on the constraints of size and space available and the user's limb length. Depending on the configuration of the various components, the connection mechanism may, in certain embodiments, extend from the signal processing unit and protrude from the distal end of the prosthetic liner. The electromechanical dock may in certain embodiments be affixed to a prosthesis shell.

Figure 13:
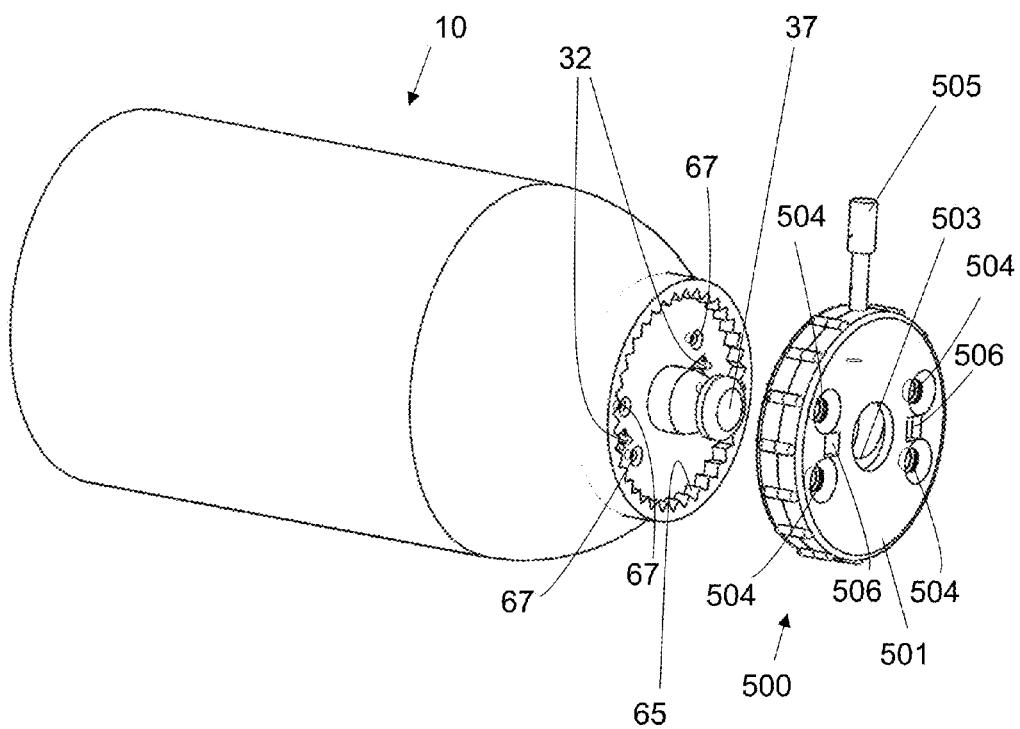
FIG. 13 illustrates an electrode assembly including a locking pin and a docking mechanism to which the locking pin may be coupled, in accordance with certain embodiments.
Figure 18:
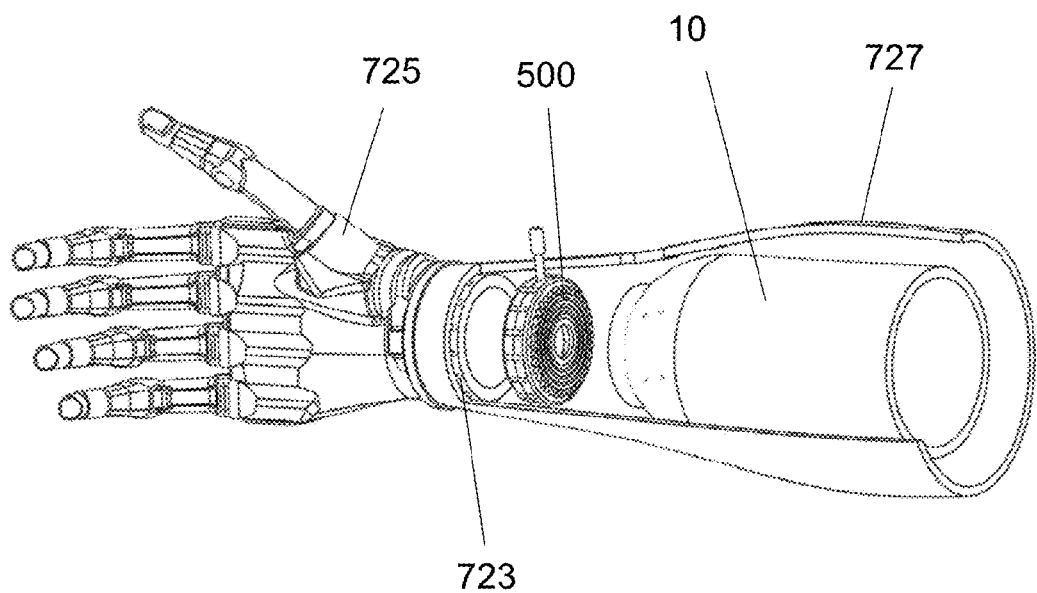
FIG. 18 illustrates components in a prosthetic arm assembly, in accordance with certain embodiments.

FIG. 13 illustrates an embodiment including a connection mechanism used to couple an electrode assembly to a docking mechanism which fits a receiving device such as, for example, a prosthetic hand. The connection mechanism in FIG. 13 is a locking pin 37 on the distal end of electrode assembly 10. The locking pin 37 is configured to be mated with electromechanical dock 500. The electrode assembly 10 may be worn over an amputee's residual limb and coupled to the remainder of the prosthesis. FIG. 18 illustrates the relative positioning of components in a prosthetic arm assembly in accordance with an embodiment, including an electrode assembly 10, a docking mechanism 500, a connector 723, a prosthetic hand 725, and a shell 727 for the prosthesis. Communication between the dock 500 and the hand 725 may be made using wired or wireless connections. In certain embodiments, the dock 500 is coupled to the shell 727 using any suitable connection mechanism, for example, an adhesive or screws.

As illustrated in FIG. 13, the locking pin 37 is sized to fit into the dock 500 and is held in place by latch 503. In addition, the dock 500 includes a plurality of threaded apertures 504 into which screws (not shown) may be positioned for holding various components of the dock 500 together. The spring-loaded pins 32 may supply an electrical connection extending from the electrode assembly 10 to the dock 500. The dock 500 also includes apertures 116 through which electrical connections may be made to a device such as the prosthetic hand 8 of FIG. 18.

Figure 14A:
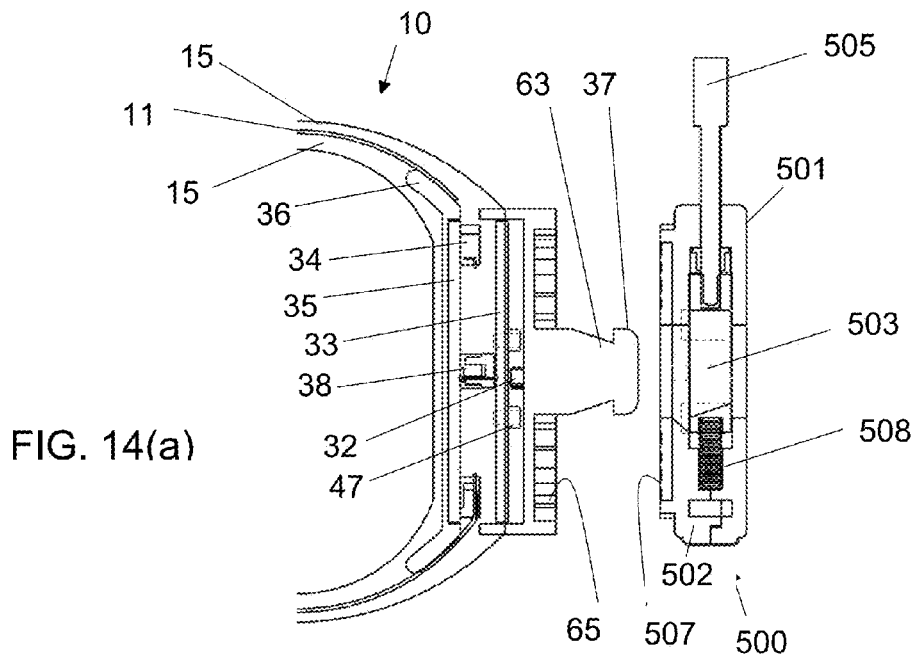
Figures 14, 14C:
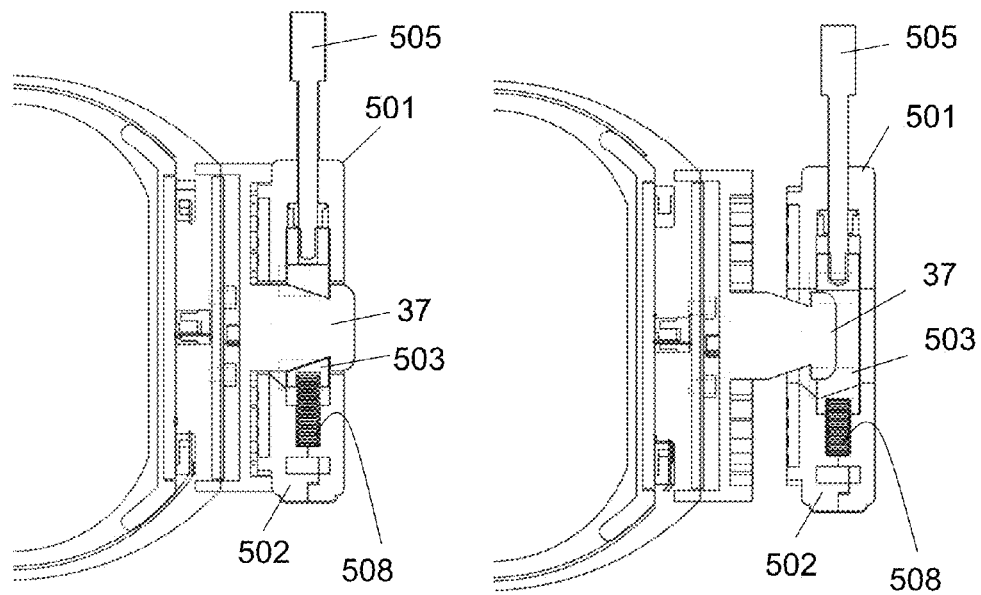

FIGS. 14(a)-14(c) illustrate an embodiment of a docking procedure for the dock and locking pin. In FIG. 14a, the locking pin 37 may be positioned adjacent to the dock 500. Various aspects of the electrode assembly described above and illustrated, for example in FIGS. 1 and 3, are also shown in FIG. 14a. Such aspects include a portion of the legs 11 and encasement 15, junction PCB 35, processing PCB 33, various components 32, 34, 38, base 36, and mounting posts 47.

As illustrated in FIG. 14b, the locking pin 37 is positioned within the dock 500 and as the locking pin 37 makes contact with a spring-loaded latch 503, the latch 503 is pushed downward and compresses the spring 508. A more detailed view of the latch 503 is illustrated in FIGS. 15(a)-15(b), which show a side cross-sectional view (FIG. 15(a)) and a transparent side angle view (FIG. 15(b)). The latch 503 includes an opening or aperture 527 sized to accept the locking pin 37. The center of the aperture 527 is indicated by the dotted arrow line in FIGS. 15a and 15b. The aperture 527 extends through the thickness of the latch 503, from a proximate side 591 (facing the electrode assembly 10) to a distal side 593 (facing a prosthetic device such as a hand). The aperture 527 is defined in part by lower surface region 595 and upper surface region 597. The lower surface region 595 extends in an upward direction from the proximate side 591 to the distal side 593. This shape acts to guide the locking pin 37 up and through the aperture 527 so that a distal end of the locking pin 37 can pass through the aperture 527 and over a portion of the distal side 593. The latch 503 also includes an opening 590 into which an actuator 505 fits and an opening 592 into which the spring 508 fits. As noted above, the application of force to the actuator 505 will cause the latch 503 to be forced down against the spring 508. This application of force may be used to remove the locking pin 37 from the latch 503, as will be described below.

As illustrated in FIG. 14(b), after the locking pin 37 has been inserted into the latch 503 (through aperture 527 in FIGS. 16(a)-(b)) and the distal end of the locking pin 37 clears the distal end of the latch 503, the latch 503 closes around a portion of the neck 63 of the locking pin 37, locking the pin 37 in place to provide mechanical stability. As illustrated in FIG. 14c, to open the latch 503 and release the locking pin 37, the user presses the actuator 505 attached to the latch 500 with a sufficient force to move the spring 508 downward a sufficient amount to open the latch 503 and allow for the locking pin 37 (and the electrode assembly 10 it is coupled to) to be removed.

Figure 16:
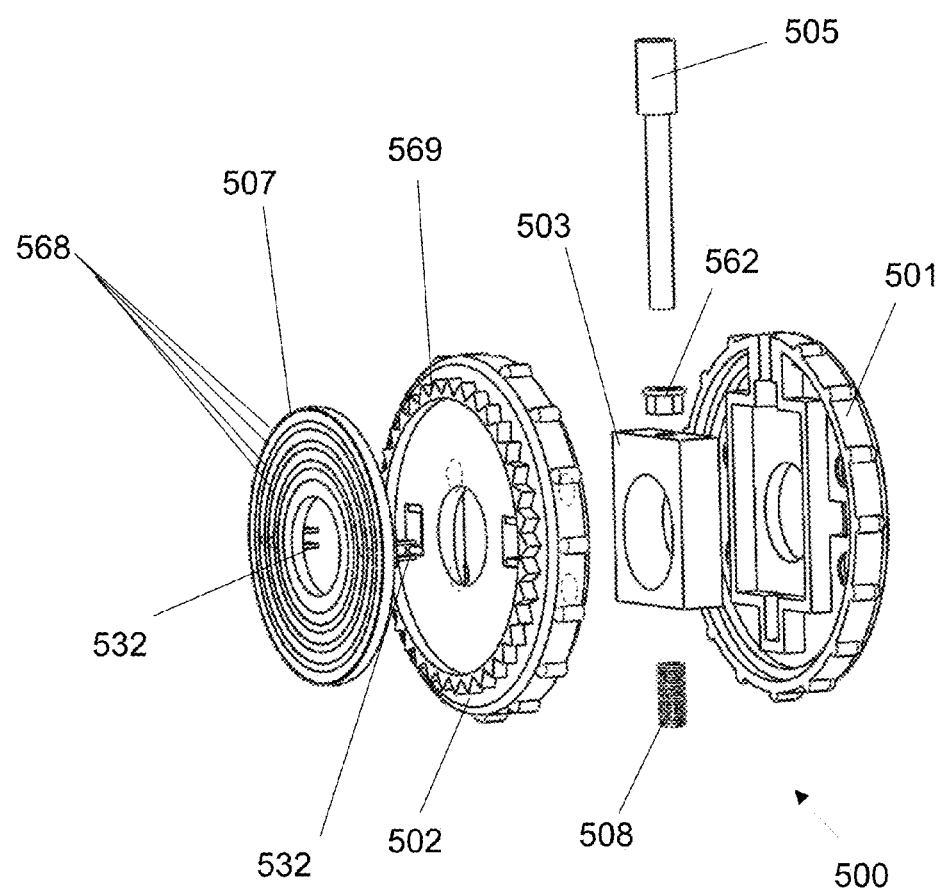
FIG. 16 illustrates features of an electromechanical dock, in accordance with certain embodiments.

FIG. 16 illustrates a view of certain components of the assembly of the electromechanical dock 500. In addition to the mechanical connection, the dock provides an electrical connection from the electrode assembly to the remainder of the prosthesis. The electrical connection may be formed by spring-loaded pins 32 (see FIG. 13) coming into contact with concentric conductive tracks 568 on a structure 507 that may take the form of, for example, a printed circuit board having the concentric conductive tracks 568 electrically insulated from one another. Four-pin connectors 532 on the backside of the structure 507 may be used to transmit the signals from the electrode assembly to the remainder of the prosthesis, through apertures 506 in the dock 500. The button 105 is positioned to extend through positioning nut 562. The latch 503 is sized to fit between the body portions 501 and 502 of the dock 500. Alignment keys 569 are positioned on body portion 502.

Certain embodiments of the electromechanical dock and electrode assembly may include mechanical keys to ensure proper alignment of the prosthesis (coupled to the dock) with the electrode assembly in the circumferential direction using a keyed mechanical connection. In these embodiments, there may be one or more keys, and the keys may take the form of teeth in a particular size and arrangement. As the number of keys is increased, there may be more possible orientations of alignment between the electrode assembly and the prosthesis. As illustrated in FIG. 13 and FIG. 16, the alignment keys 65, 569 are triangular in shape and adapted to fit together to provide a secure fit between the dock and electrode assembly. Other embodiments may include more or less keys and may be formed in different shapes, including, but not limited to, rectangles and hemispheres.

Figure 17:
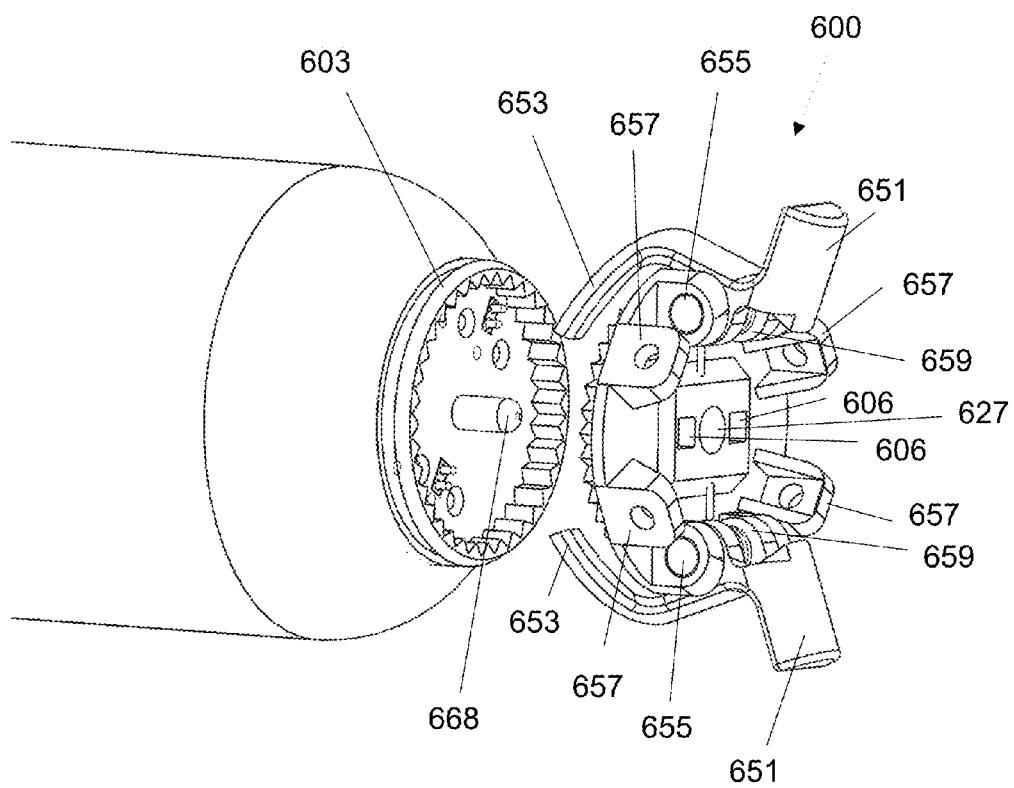
FIG. 17 illustrates an electromechanical dock with a two finger release mechanism, in accordance with certain embodiments.

FIG. 17 illustrates another embodiment of an electromechanical dock 600 with a two finger release mechanism. In this embodiment, two spring-loaded, hemispheric latches 653 close around a neck portion 603 of the electrode assembly that is adapted to receive the latches 653. Two torsional springs 659 located at an axle 655 securing the latches 653 to the dock provide the spring-force to keep the latches 653 closed. The alignment structure 668 extends outward from the electrode assembly and into the aperture 627 in the dock 600. The two lever arms 651 may be pressed sufficiently inward to open the latches 653. Mounting structures 657 are used to couple the dock 600 to a prosthetic shell. Electrical connections to a device such as a prosthetic hand may be made through apertures 606.

Various embodiments may have one or more of the following advantages, including: (i) the ability to obtain a more accurate control over a prosthetic device such as a hand due to the additional information that can be processed through the use of more than two myoelectric electrodes; (ii) the ability to form a removeable yet close fitting electrode assembly including a prosthetic liner that encases an electrode support structure; and (iii) the ability to remove the processing circuitry from the rest of the assembly without disturbing the electrodes.

Terms such as "first", "second", and the like as used herein to not necessarily denote any particular order, quantity, or importance, but are used to distinguish one element from another. Terms such as "upper" and "lower" are used to refer to the relative position of features as illustrated in the figures.

While certain exemplary embodiments have been described above and shown in the accompanying drawings, it is to be understood that such embodiments are merely illustrative and not restrictive, and that embodiments are not restricted to the specific constructions and arrangements shown and described since modifications may occur to those having ordinary skill in the art. For example, while the use of wired connections between components are described in certain embodiments, wireless communication may alternatively be used. In another example, while an amplifier may be positioned in the signal processing unit in certain embodiments, other embodiments may include an amplifier positioned on the back side of the electrode contacts. In one such example, where an electrode includes three contacts, with one side of each of the contacts exposed to contact the skin of a user, the other side of each of the contacts is coupled to an amplifier (one amplifier for three contacts).

What is claimed:

1. An assembly comprising:
   a plurality of electrode contacts adapted to receive myoelectric signals from a body when placed into contact with the body;
   a support structure adapted to support the electrode contacts, the support structure comprising a plurality of legs, each leg comprising a flexible body on which one or more electrode contacts are positioned and an electrically conductive path for each electrode contact;
   a prosthetic liner;
   the support structure being positioned on the prosthetic liner; and
   signal processing circuitry adapted to process the myoelectric signals from the body;
   wherein the legs are adapted to deliver the myoelectric signals from the electrodes to the signal processing circuitry.

2. The assembly of claim 1 wherein the legs each include a plurality of the electrode contacts electrically coupled thereto.

3. The electrode assembly of claim 1, wherein the legs and prosthetic liner are sufficiently flexible to enable the legs and the prosthetic liner to be rolled up when removing the electrode assembly from a limb and then unrolled when positioning the electrode assembly on a limb.

4. The assembly of claim 1, wherein the signal processing circuitry is coupled to a board, the board being removably coupled to the assembly.

5. The assembly of claim 1, wherein the legs each include a plurality of locations on which an electrode contact may be positioned.

6. The assembly of claim 1, wherein the legs are integrally formed with one another.

7. The assembly of claim 1, wherein the electrode legs are individually removably coupled to the assembly.

8. An assembly comprising:
   a plurality of electrode contacts adapted to receive myoelectric signals from a body when placed into contact with the body;
   a support structure adapted to support the electrode contacts;
   the support structure being embedded in an encasement;
   a housing to which the support structure is coupled, the support structure and the housing adapted to be positioned to form a loop around an appendage;
   the electrode contacts extending through openings in the encasement; and
   signal processing circuitry adapted to process the myoelectric signals from the body, the signal processing circuitry positioned in the housing.

9. The assembly of claim 8, the support structure adapted to pass signals from the electrode contacts to the signal processing circuitry.

10. The assembly of claim 8, the support structure comprising two band-like sections, each of the band-like sections coupled to the housing.

11. The assembly of claim 10, further comprising a connection mechanism coupled to the band-like sections, the connection mechanism adapted to couple the band-like sections together to close around an appendage.

12. An assembly comprising:
- a plurality of electrode contacts adapted to receive myoelectric signals from a body when placed into contact with the body;
- a support structure adapted to support the electrode contacts, the support structure comprising a plurality of legs, each leg comprising a flexible body on which one or more electrode contacts are positioned and an electrically conductive path for each electrode contact;
- a prosthetic liner;
- the support structure being positioned on the prosthetic liner;
- signal processing circuitry adapted to process the myoelectric signals from the body;
- wherein the legs are adapted to deliver the myoelectric signals from the electrodes to the signal processing circuitry;
- a docking structure;
- a receiving device;
- wherein the docking structure is adapted to be electrically coupled to the signal processing circuitry;
- wherein the docking structure is adapted to be electrically coupled to the receiving device; and
- wherein the docking structure is adapted to be positioned between the prosthetic liner and the receiving device.

13. The assembly of claim 12, further comprising a shell for a prosthesis, the shell positioned over the prosthetic liner, wherein the docking mechanism includes an actuator extending through the shell.

14. The assembly of claim 12, further comprising a connector extending from the prosthetic liner, wherein the docking mechanism is mechanically coupled to the connector.

15. The assembly of claim 1, wherein the prosthetic liner has a structure selected from the group consisting of: (i) a single layer encasement, and (ii) a two layer encasement, the two layer encasement including an inner encasement layer and an outer encasement layer.

16. The assembly of claim 15, wherein the prosthetic liner includes the single encasement layer and the legs are embedded in the single layer encasement.

17. The assembly of claim 15, wherein the prosthetic liner includes the two layer encasement and the plurality of legs extend between the inner encasement layer and the outer encasement layer.

* * * * *

UNITED STATES PATENT AND TRADEMARK OFFICE
CERTIFICATE OF CORRECTION

PATENT NO. : 8,591,599 B1  
APPLICATION NO. : 12/987035  
DATED : November 26, 2013  
INVENTOR(S) : Kaliki et al.

Page 1 of 1

It is certified that error appears in the above-identified patent and that said Letters Patent is hereby corrected as shown below:

In the Specification

Column 1, line 4, please insert the following new paragraph -- This invention was made with government support under Grant No. 5R44NS065495 awarded by NIH (National Institutes of Health). The government has certain rights in the invention. --

In the Claims

Column 16, Claim 16, line 17, please delete "encasement layer" and insert -- layer encasement -- in its place.

Signed and Sealed this  
Fourteenth Day of April, 2015

Michelle K. Lee  
*Director of the United States Patent and Trademark Office*